United States Patent
Minoda et al.

(10) Patent No.: US 9,726,650 B2
(45) Date of Patent: *Aug. 8, 2017

(54) CHROMATOGRAPHIC MEDIUM

(71) Applicant: DAICEL CORPORATION, Osaka-shi, Osaka (JP)

(72) Inventors: Toshiharu Minoda, Myoko (JP); Isamu Ikeda, Myoko (JP)

(73) Assignee: DAICEL CORPORATION, Osaka-shi, Osaka (JP)

( * ) Notice: Subject to any disclaimer, the term of this patent is extended or adjusted under 35 U.S.C. 154(b) by 465 days.

This patent is subject to a terminal disclaimer.

(21) Appl. No.: 14/375,677

(22) PCT Filed: Feb. 1, 2013

(86) PCT No.: PCT/JP2013/052324
§ 371 (c)(1),
(2) Date: Jul. 30, 2014

(87) PCT Pub. No.: WO2013/115350
PCT Pub. Date: Aug. 8, 2013

(65) Prior Publication Data
US 2014/0374333 A1    Dec. 25, 2014

(30) Foreign Application Priority Data
Feb. 3, 2012    (JP) ................... 2012-022004

(51) Int. Cl.
*B01D 15/08*    (2006.01)
*G01N 30/93*    (2006.01)
(Continued)

(52) U.S. Cl.
CPC ............ *G01N 30/92* (2013.01); *B01D 15/08* (2013.01); *B01J 20/291* (2013.01); *G01N 30/93* (2013.01);
(Continued)

(58) Field of Classification Search
CPC ........ B01D 15/08; G01N 30/90; G01N 30/92; G01N 30/93; G01N 30/94;
(Continued)

(56) References Cited

U.S. PATENT DOCUMENTS 3,591,805 A * 7/1971 Schoeffel ............... G01N 30/92
210/198.3
3,623,841 A    11/1971 Kraffczyk et al.
(Continued)

FOREIGN PATENT DOCUMENTS

DE    1 909 058 A1    9/1969
EP    0 014 956 A1    9/1980
(Continued)

OTHER PUBLICATIONS

Extended European Search Report issued in corresponding European Application No. 13744353.7, dated Sep. 15, 2015 (5 pages).
(Continued)

*Primary Examiner* — Katherine Zalasky
(74) *Attorney, Agent, or Firm* — Flynn, Thiel, Boutell & Tanis, P.C.

(57) ABSTRACT

A chromatographic medium having a separating agent layer, which is used to separate target substances, a filling agent layer, which is used to fix the target substances before the target substances are separated, and a permeation layer, which is used to enable permeation of the target substances separated by the separating agent layer, wherein the filling agent layer comes into contact with the separating agent layer via a plane that intersects the direction of development of the target substances in the chromatographic medium and is positioned on the upstream side in the direction of development, the separating agent layer exhibits separability of the target substances and optical responsiveness to ultraviolet rays, and the permeation layer exhibits an optical responsiveness that is different from those of the target substances and the separating agent layer.

19 Claims, 5 Drawing Sheets

(a)

(b)

(c)

(51) Int. Cl.
*G01N 30/92* (2006.01)
*B01J 20/291* (2006.01)
*B01J 20/32* (2006.01)
*B01J 20/285* (2006.01)
*G01N 30/94* (2006.01)
*G01N 30/88* (2006.01)

(52) U.S. Cl.
CPC ........ *B01J 2220/46* (2013.01); *B01J 2220/54* (2013.01); *G01N 2030/8877* (2013.01); *G01N 2030/945* (2013.01)

(58) Field of Classification Search
CPC ....... G01N 2030/945; G01N 2030/8877; B01J 20/291; B01J 2220/80
See application file for complete search history.

(56) References Cited

U.S. PATENT DOCUMENTS

| | | | |
|---|---|---|---|
| 4,158,626 A | | 6/1979 | Halpaap et al. |
| 4,313,906 A | * | 2/1982 | Filipi ............... G01N 30/92 210/198.3 |
| 4,786,415 A | * | 11/1988 | Shibata ............ B01D 15/08 210/198.2 |
| 5,306,645 A | | 4/1994 | Yamamoto et al. |
| 5,773,576 A | | 6/1998 | Junker-Buchheit et al. |
| 6,787,366 B1 | * | 9/2004 | Novak ............... G01N 31/22 210/634 |
| 2001/0051350 A1 | * | 12/2001 | Nazareth ........... G01N 33/558 435/7.5 |
| 2013/0067996 A1 | | 3/2013 | Minoda et al. |

FOREIGN PATENT DOCUMENTS

| | | |
|---|---|---|
| EP | 2 579 034 A1 | 4/2013 |
| GB | 1 264 535 A | 2/1972 |
| JP | 53-149393 A | 12/1978 |
| JP | 03-063567 A | 3/1991 |
| JP | 3140138 B2 | 3/2001 |
| WO | WO 2011/106694 A1 | 9/2011 |
| WO | WO 2011/149041 A1 | 12/2011 |

OTHER PUBLICATIONS

English translation of International Preliminary Report on Patentability and Written Opinion of the International Searching Authority for PCT/JP2013/052324 (6 pgs.).
International Search Report for PCT/JP2013/052324 (3 pgs.).

\* cited by examiner (a)      (b)

(a)      (b)

(1)  (2)

(1)  (2)  (3)  (4)

CHROMATOGRAPHIC MEDIUM

TECHNICAL FIELD

The present invention relates to a chromatographic medium at least having two layers having different optical responsiveness to ultraviolet rays, and further having another layer.

BACKGROUND ART

Thin layer chromatography (hereinafter also referred to as "TLC") is known as a method for separating and detecting specific components in a mixture. When separating components by means of TLC, detection is achieved by subjecting spots, which are obtained by developing a sample, to irradiation with ultraviolet rays or to a coloration treatment using a coloring reagent on the basis of differences in optical responsiveness of, for example, a separating agent layer and the components being detected.

Meanwhile, separating agents that contain polysaccharide derivatives such as phenyl esters of polysaccharides are known as separating agents for optical isomers. When used in separating agent layers for TLC plates, such separating agents that contain aromatic rings are, in some cases, unable to detect components to be detected when irradiating with ultraviolet rays or carrying out coloration treatment using a coloring reagent.

As means for solving this type of problem, a TLC plate is known in which a first separating agent layer, which can achieve separation of target substances but does not exhibit an optical responsiveness, and a second separating agent layer, which does not achieve a separation function but exhibits an optical responsiveness, are formed side-by-side on the same substrate (for example, see patent document 1). In this TLC plate, target substances are developed from the first separating agent layer to the second separating agent layer, spots separated by the first separating agent layer migrate to the adjacent second separating agent layer and are detected there according to their optical responsiveness.

In this TLC plate, the extract component that is readily adsorbed by the first separating agent layer does not, in some cases, satisfactorily reach the second separating agent layer. In addition, because the speed of migration of a spot generally varies in each separating agent layer, the positional relationship of spots in a first separating agent layer is not necessarily precisely maintained in a second separating agent layer. Therefore, it is not necessarily possible to precisely detect the state of separation in the first separating agent layer in the aforementioned TLC plate, and further research is needed in this respect at least.

Patent Document 1: Japanese Patent No. 3140138

DISCLOSURE OF THE INVENTION

The present invention provides a chromatographic medium which can separate and detect target substances using a single kit.

The inventors of the present invention found that it was possible to solve the aforementioned problems by using a chromatographic medium having a separating agent layer, which is used to separate target substances, a filling agent layer, which is used to fix the aforementioned target substances before the aforementioned target substances are separated, and a permeation layer, which is used to enable permeation of the target substances separated by the aforementioned separating agent layer, wherein the aforementioned filling agent layer comes into contact with the aforementioned separating agent layer via a plane that intersects a direction of development of the aforementioned target substances in the aforementioned chromatographic medium and is positioned on the upstream side in the aforementioned direction of development, the aforementioned separating agent layer exhibits a separability of the target substances and exhibits an optical responsiveness to ultraviolet rays, and the aforementioned permeation layer exhibits an optical responsiveness that is different from those of the aforementioned separating agent layer, and thereby completed the present invention.

Specifically, the present invention provides the following.

<1> A chromatographic medium having a separating agent layer, which is used to separate target substances, a filling agent layer, which is used to fix the target substances before the target substances are separated, and a permeation layer, which is used to enable permeation of the target substances separated by the separating agent layer, wherein the filling agent layer comes into contact with the separating agent layer via a plane that intersects a direction of development of the target substances in the chromatographic medium and is positioned on the upstream side in the direction of development, the separating agent layer exhibits separability of the target substances and exhibits an optical responsiveness to ultraviolet rays, and the permeation layer exhibits an optical responsiveness that is different from those of the target substances and the separating agent layer.

<2> The chromatographic medium according to <1>, wherein the filling agent layer is laminated in a region of the chromatographic medium extending from a dip end part, which is dipped in a developing solution used to develop the target substances, and having a length which is 1/20 to 1/2 of the length of the chromatographic medium in the direction of development.

<3> The chromatographic medium according to <1> or <2>, wherein the permeation layer is laminated in a discontinuous manner in the direction of development of the chromatographic medium.

<4> The chromatographic medium according to any one of <1> to <3>, wherein the permeation layer is laminated in the form of dots on the separating agent layer.

<5> The chromatographic medium according to <4>, wherein in the permeation layer laminated in the form of dots, the average diameter of the dots is 0.01 to 5 mm and the pitch between dots is 0.015 to 5 mm.

<6> The chromatographic medium according to any one of <1> to <3>, wherein the permeation layer is laminated on the separating agent layer as band-like rows that intersect a direction of development of the chromatographic medium.

<7> The chromatographic medium according to <6>, wherein bands that form the band-like rows are selected from among straight lines, wavy lines and dashed lines thereof.

<8> The chromatographic medium according to any one of <1> to <7>, wherein the permeation layer is thinner than the separating agent layer.

<9> The chromatographic medium according to any one of <1> to <8>, wherein a separating agent that constitutes the separating agent layer is a separating agent for optical isomers.

<10> The chromatographic medium according to <9>, wherein the separating agent for optical isomers contains a polysaccharide derivative formed of a polysaccharide and one type of group selected from aromatic ester groups, aromatic carbamoyl groups, aromatic ether groups or carbonyl groups that replace some or all of the hydroxyl groups or amino groups in the polysaccharide.

<11> The chromatographic medium according to any one of <1> to <10>, wherein the permeation layer contains a porous material and a fluorescent indicator or coloring reagent as constituent materials.

<12> The chromatographic medium according to any one of <1> to <12>, wherein the filling agent layer contains a porous material as a constituent material.

<13> The chromatographic medium according to <11> or <12>, wherein the porous material is silica gel or surface-treated silica gel.

<14> The chromatographic medium according to any one of <11> to <13>, further comprising a binder as a constituent material.

<15> The chromatographic medium according to any one of <1> to <14>, wherein scale marks and/or characters are present on the permeation layer.

<16> The chromatographic medium according to <15>, wherein the scale marks and/or characters exhibit an optical responsiveness that are different from those of the permeation layer.

<17> The chromatographic medium according to any one of <1> to <16>, having a base material which faces the separating agent layer or the permeation layer and which supports the chromatographic medium.

<18> The chromatographic medium according to any one of <1> to <17>, wherein the chromatographic medium is plate-shaped, cylindrical or columnar.

<19> A TLC plate having the chromatographic medium according to any one of <1> to <16>, and a base material used to support the chromatographic medium, wherein the chromatographic medium is laminated on a plurality of regions on the base material.

<20> A TLC material formed of the chromatographic medium according to any one of <1> to <16>, and a base material used to support the chromatographic medium.

In the chromatographic medium of the present invention, the permeation layer, which is used to enable permeation of the separated target substances, is laminated so as to face the separating agent layer, and because this permeation layer exhibits an optical responsiveness that is different from those of the separating agent layer, target substances present in a separating agent layer, which cannot be detected by means of optical responsiveness and which exhibit the same optical responsiveness as the separating agent layer, permeate into the permeation layer and can therefore be detected by means of the optical responsiveness of the target substances that permeate into the permeation layer.

In the chromatographic medium of the present invention, the filling agent layer comes into contact with the aforementioned separating agent layer via a plane that intersects the direction of development of the aforementioned target substances in the aforementioned chromatographic medium and is positioned on the upstream side in the aforementioned direction of development. As a result, when the aforementioned target substances are developed after being fixed in the part that contains this filling agent layer, the target substances are temporarily concentrated at the separating agent layer side of the boundary between the filling agent layer and the separating agent layer due to the filling agent layer and separating agent layer exhibiting different holding powers for the target substances. In addition, because separation of the target substances subsequently occurs in the separating agent layer, spots of the target substances are formed in such a way that detection of the target substances can be reliably achieved even if the concentration of target substances is low in the solution that contains the target substances to be applied as spots. Furthermore, the target substance separation performance is improved.

In addition, because the chromatographic medium of the present invention can achieve separation and detection of target substances using a single kit, without the need for other components, a complicated procedure is not required to separate and detect the target substances.

MODE FOR CARRYING OUT THE INVENTION

Figure 1:
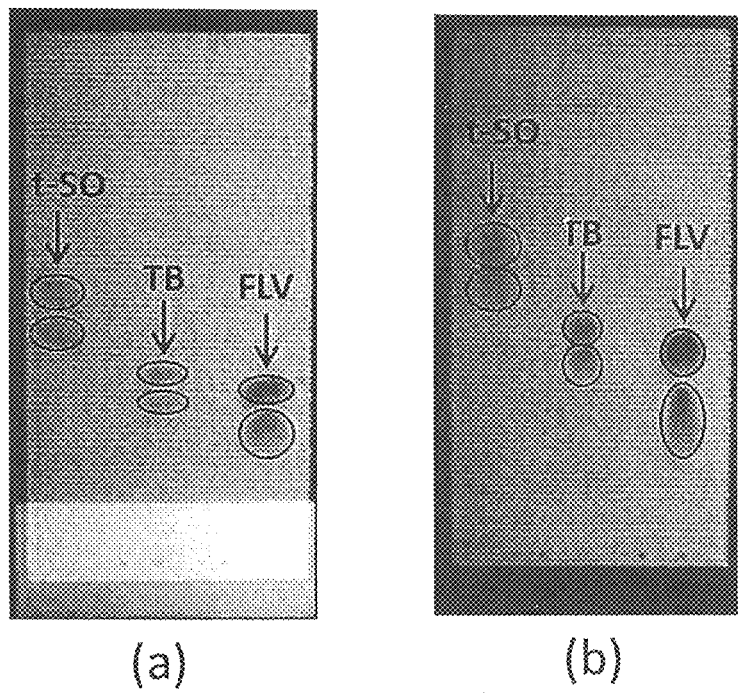
FIG. 1(a) is a drawing (photograph) showing spots obtained by using the TLC plate produced in Example 1 (the region with a length of 2.0 cm from the developing solution dip end part was obtained by laminating with the filling agent layer and laminating the permeation layer on the filling agent layer) and developing trans-stilbene oxide (t-SO), Tröger's base and a flavanone using hexane/ethanol (90:10, v/v) as a developing solution.
FIG. 1(b) is a photograph obtained by carrying out the same procedure as that carried out in Example 1, except that the TLC plate produced in Comparative Example 1 was used.
Figure 2:
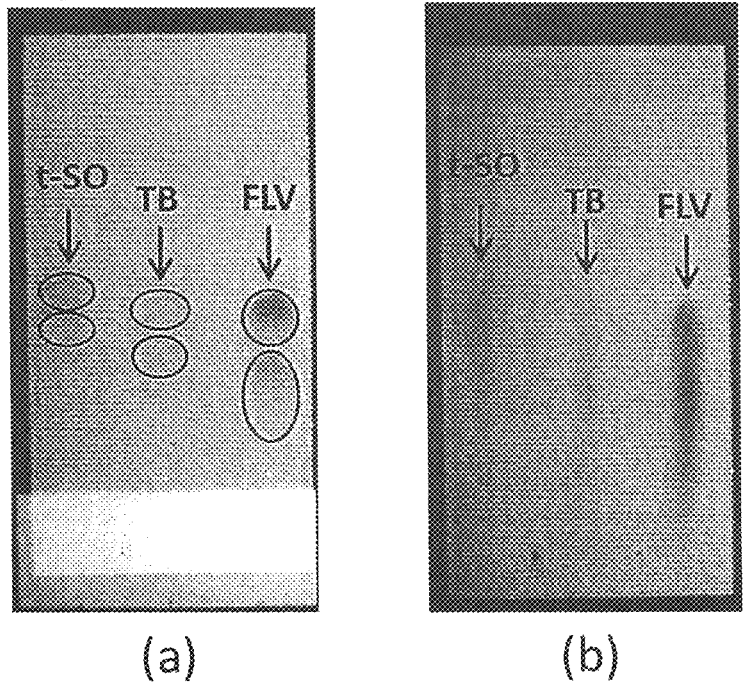
FIG. 2(a) is a drawing (photograph) showing spots obtained by using the same TLC plate as that produced in Example 1 and developing the same target substances as those in Example 1 using methanol as a developing solution (Example 2)
FIG. 2(b) is a photograph obtained by carrying out the same procedure as that carried out in Example 2, except that the TLC plate produced in Comparative Example 2 was used.

The chromatographic medium of the present invention has a separating agent layer, a filling agent layer that is used to fix target substances before the target substances are separated, and a permeation layer that is used to enable permeation of the target substances separated by the separating agent.

In the chromatographic medium of the present invention, the above-mentioned separating agent layer is laminated with a filling agent layer that comes into contact with the aforementioned separating agent layer via a plane that intersects the direction of development of the aforementioned target substances in the aforementioned chromatographic medium, a permeation layer is laminated so as to face the above-mentioned separating agent layer, and encompasses plate-shaped, cylindrical and columnar chromatograph media, with a plate-shaped chromatographic medium being a so-called thin layer chromatography (TLC) medium. Meanwhile, cylindrical or columnar chromatograph media are also known as stick columns.

In addition, the aforementioned separating agent layer exhibits a separability of the target substances and also exhibits an optical responsiveness to ultraviolet rays. Meanwhile, the aforementioned permeation layer exhibits an optical responsiveness to ultraviolet rays that are different from those of the target substances and the separating agent layer.

Examples of target substances used in the present invention include optical isomers. Exhibiting a separability of target substances means having the capacity to separate the target substances and, in cases where the target substances are optical isomers, means exhibiting optical resolution properties. In addition, in the present invention, an optical responsiveness to ultraviolet rays means luminescence caused by ultraviolet rays, such as fluorescence, or the absorption of ultraviolet rays.

Moreover, in the chromatographic medium of the present invention, the filling agent layer comes into contact with the aforementioned separating agent layer via a plane that intersects the direction of development of the aforementioned target substances, but in the present invention, "intersects" does not necessarily mean an exact right angle (90°) relative to the direction of development of the aforementioned target substances, and may mean an inclination or form within a range whereby separation of the target substances is not affected.

This range may be 88° to 92° relative to the direction of development of the aforementioned target substances, for example.

By having the separating agent layer and permeation layer as described above, the chromatographic medium of the present invention enables the target substances that have been separated by the separating agent layer to permeate into the permeation layer. In addition, because the optical responsiveness of the permeation layer differ from the optical responsiveness of the target substances and the separating agent layer, it is possible to verify the target substances that have permeated into the permeation layer by irradiating with ultraviolet rays or the like.

In addition, in the chromatographic medium of the present invention, the filling agent layer comes into contact with the separating agent layer via a plane that intersects the direction of development of the aforementioned target substances in the aforementioned chromatographic medium. In addition, the positional relationship is such that the separating agent layer is laminated on the downstream side in the direction of development of the chromatographic medium and the filling agent layer is laminated on the upstream side in the direction of development of the chromatographic medium.

By having such a positional relationship, the target substances are temporarily concentrated at the separating agent layer side of the boundary between the filling agent layer and the separating agent layer when developing the target substances that are fixed in the filling agent layer. The target substances are subsequently separated by interactions with the separating agent layer. As a result, even if the concentration of the target substances to be developed is low, because the concentration occurs in the vicinity of the aforementioned boundary, spots able to be subsequently visually confirmed are formed.

In addition, because the target substances are temporarily concentrated in the vicinity of the boundary with the separating agent layer, it is possible to minimize broadening of the spots of the target substances when the target substances are separated.

Moreover, the region of the filling agent layer in the aforementioned chromatographic medium includes a region in which only separation of the target substances by the separating agent layer and confirmation of the target substances in the permeation layer can be achieved, and if a region in which the fixing of the target substances is possible is present in the region of this filling agent layer, the size and shape thereof is not limited.

From the perspective of ensuring the satisfactory separation of the target substances, it is preferable for the aforementioned filling agent layer to be present in the region of the aforementioned chromatographic medium extending from a dip end part (hereinafter also referred to as the bottom edge), which is dipped in the developing solution used to develop the aforementioned target substances, and having a length which is half the length of the chromatographic medium in the direction of development.

From the perspective of ensuring a good separation of the target substances, it is more preferable for the aforementioned filling agent layer to be the region extending from the bottom edge of the aforementioned chromatographic medium and having a length which is 1/40 to 1/2, particularly preferably 1/20 to 1/2.2 of the length of the chromatographic medium in the direction of development. The boundary between the aforementioned separating agent layer and the filling agent layer is provided further downstream in the direction of development than the spotting positions of the target substances and the dipping position when the chromatographic medium is dipped in the developing bath.

In addition, from the perspective of productivity, it is preferable for the shape of the filling agent layer, when viewed from the direction in which the target substances are applied as spots, to be a square shape that includes the bottom edge in cases where the chromatographic medium is plate-shaped. In addition, in cases where the shape of the plate, when viewed from the direction in which the target substances are applied as spots, is triangular and the apex part of the triangle is dipped in the developing bath, the filling agent layer has an inverted triangular shape that includes this apex part.

Alternatively, the aforementioned filling agent layer may be in the form of an approximate circle having a size whereby spotting of the target substances is possible.

In addition, if the region in which the aforementioned permeation layer is laminated faces at least the aforementioned separating agent layer, the region in which the aforementioned permeation layer is laminated does not need to be the entire region of the separating agent layer, and as long as the target substances can be confirmed, the permeation layer may not be laminated on a part of the above-mentioned separating agent layer.

In addition, the permeation layer may be laminated so as to face the filling agent layer in addition to facing the separating agent layer.

From the perspective of being able to confirm the separation of a wide variety of target substances, the ratio of the area of the region in which the permeation layer is laminated relative to the total area of the separating agent layer is preferably 5% to 90%, more preferably 10% to 80%, and further preferably 20% to 70%.

This type of region in which the permeation layer is not laminated and the separating agent layer is exposed can be obtained by laminating the separating agent layer and then, when laminating the permeation layer by using the coating techniques, dipping techniques or printing techniques described later, not coating, dipping or printing only this region.

Alternatively, this type of region can be obtained by laminating the permeation layer on the whole of the separating agent layer and then removing the permeation layer from the separating agent layer by means of a procedure such as scraping.

Meanwhile, in cases where the permeation layer is laminated so as to face the filling agent layer also, the ratio of the area of the permeation layer on the filling agent layer is not particularly limited, and the permeation layer can be laminated at an arbitrary areal proportion.

Moreover, the filling agent layer and the permeation layer can be constituted from the same material, as mentioned later, and in such cases, the filling agent layer and the permeation layer are regarded as consisting of two layers for the sake of convenience, but form a single layer in reality.

If the chromatographic medium of the present invention has a constitution such as that described above, the shape thereof is not particularly limited, and can be plate-shaped, cylindrical or columnar.

An example of a plate-shaped chromatographic medium is one having a first embodiment, in which a material such as that described later is used as a base material, the permeation layer, the separating agent layer, the filling agent layer and the base material are laminated in that order when viewed from the direction in which ultraviolet rays is irradiated, and the permeation layer is laminated so as to face the separating agent layer only (see FIG. 6(a)), a second embodiment, in which the permeation layer, the separating agent layer, the filling agent layer and the base material are laminated in that order when viewed from the direction in which ultraviolet rays is irradiated and the permeation layer is laminated so as to face the separating agent layer and the filling agent layer (see FIG. 6(b)), or a third embodiment, in which the base material, the permeation layer, the separating agent layer and the filling agent layer are laminated in that order when viewed from the direction in which ultraviolet rays is irradiated (see FIG. 6(c)).

In the aforementioned first embodiment, spotting of the target substances occurs in the region where the filling agent layer is exposed on the surface that is irradiated with ultraviolet rays.

In the aforementioned second embodiment, spotting of the target substances occurs in the region where the permeation layer is laminated on the filling agent layer.

Figure 6:
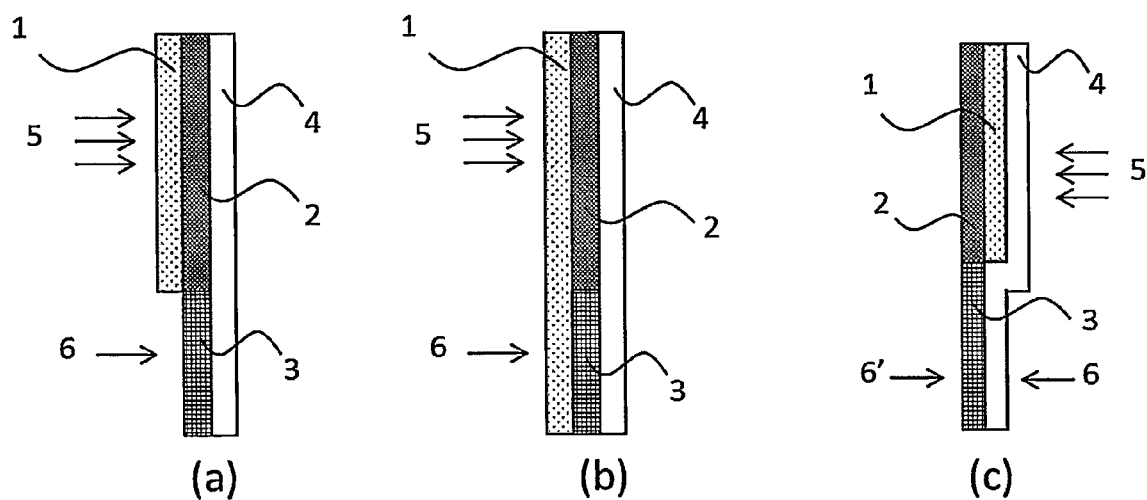
FIG. 6(a) is a schematic view showing a cross-section of one embodiment of the plate-like shape of the chromatographic medium of the present invention.
FIG. 6(b) is a schematic view showing a cross-section of another embodiment of the plate-like shape of the chromatographic medium of the present invention.
FIG. 6(c) is a schematic view showing a cross section of another embodiment of the plate-like shape of the chromatographic medium of the present invention.

A flexible material such as that shown in FIG. 6(c) is used as the base material in the aforementioned third embodiment, and forming the base material so as to be in contact with the filling agent layer and the permeation layer, as shown in FIG. 6(c), is preferred from the perspective of preventing the filling agent layer and permeation layer from disintegrating.

In addition, in the aforementioned third embodiment, spotting of the target substances can occur from the direction opposite to the direction in which ultraviolet rays is irradiated, as shown in FIG. 6(c) (6' in FIG. 6(c)), but it is also possible to remove a part of the base material and carry out spotting from the same direction as the direction in which the ultraviolet rays is irradiated (6 in FIG. 6(c)).

In cases where the chromatographic medium of the present invention is a plate-shaped TLC medium, the aforementioned base material can be a publicly known base material used in TLC plates. Examples of such base materials include glass, resin, metal and paper plates. The shape of the base material is not particularly limited, but rectangular plates commonly used in TLC are preferred.

Figure 7:
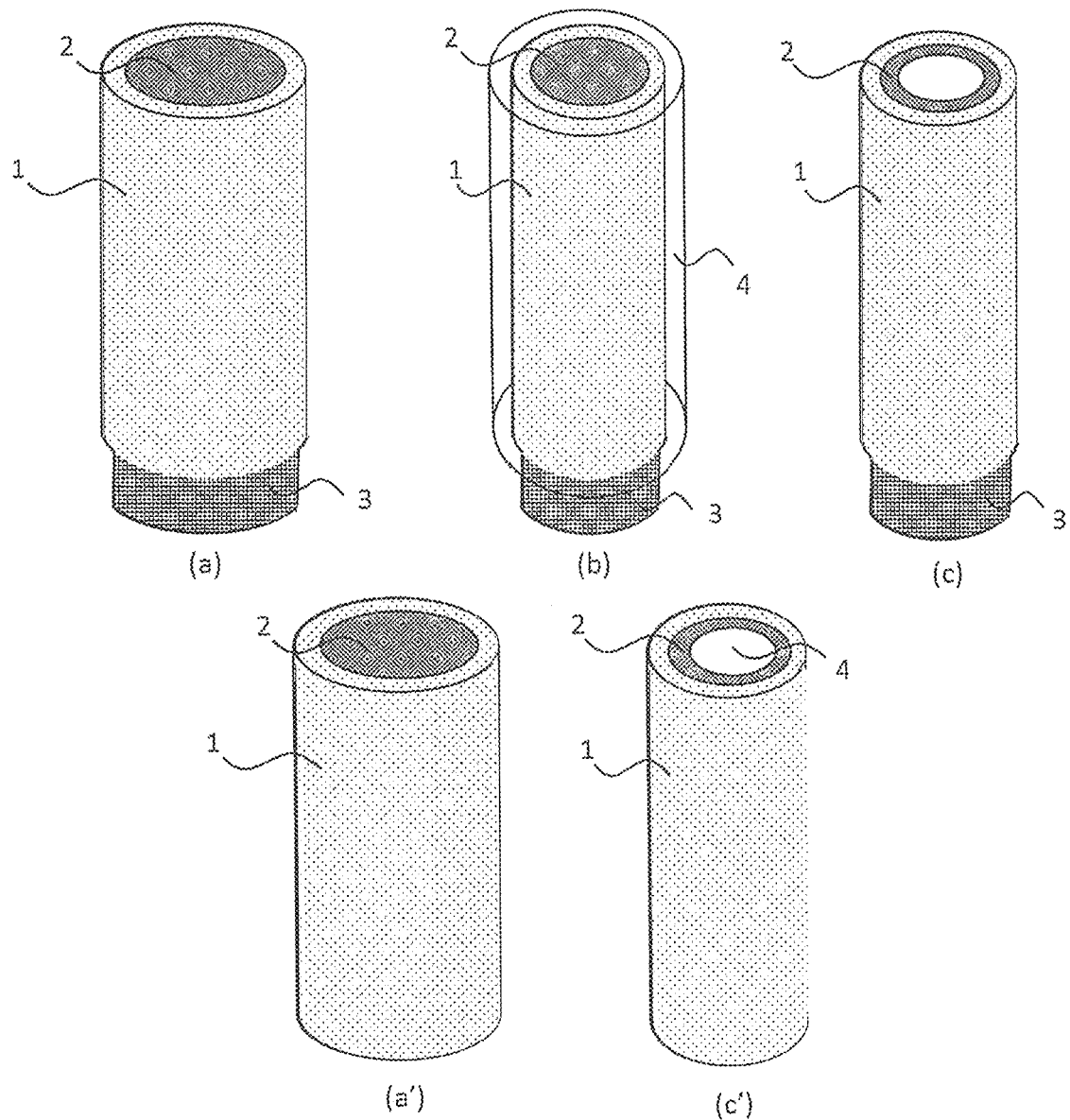
FIG. 7 is a schematic view showing one embodiment of a columnar shape (FIGS. 7(a), 7(b), and 7(a')) and a cylindrical shape (FIGS. 7(c) and 7(c')) of the chromatographic medium of the present invention.

Meanwhile, examples of cylindrical and columnar chromatograph media include those shown in FIG. 7. In these examples, the shape of the cross-section in a direction perpendicular to the axis is elliptical or circular, but this shape is not limited to these, and may be polygonal. These embodiments include embodiments in which the separating agent layer, the filling agent layer and the permeation layer are formed on the outer peripheral surface of a columnar or cylindrical base material and embodiments in which the separating agent layer, the filling agent layer and the permeation layer are formed on the inner peripheral surface of a cylindrical base material.

A columnar base material can be, for example, a rod having a polygonal or circular cross-sectional shape, and a cylindrical base material can be, for example, a tube having a polygonal or circular cross-sectional shape, a column tube or a tube having the same dimensions as a column tube.

In cases where the separating agent layer, the filling agent layer and the permeation layer are laminated on the inner peripheral surface of a cylindrical base material, it is possible to verify target substances by using a light-transmissive base material as the cylindrical base material. Here, light-transmissive means a degree of transparency by which it is possible to verify the optical characteristics (coloration, luminescence, light absorption and so on) of spots of the target substances. Examples of tubes such as column tubes having such light transmission properties include quartz glass tubes and tubes made from fluororesins such as PFA (tetrafluoroethylene-perfluoroalkyl vinyl ether copolymers).

In addition, it is possible to obtain a liquid-permeable chromatographic medium which is formed only of a separating agent layer, a filling agent layer and a permeation layer and which does not have a base material.

In the cylindrical or columnar chromatograph media shown in FIG. 7 also, the target substances are spotted in the region in which the filling agent layer is exposed ((a) to (c) in FIG. 7), or in the region of the permeation layer laminated on the filling agent layer ((a') and (c') in FIG. 7).

This type of cylindrical or columnar chromatographic medium generally has a length of 1 to 40 cm and a diameter (maximum diameter) of 0.1 to 1 cm.

The separating agent used in the separating agent layer in the chromatographic medium of the present invention is not particularly limited as long as the agent exhibits a separability of the target substances and exhibits an optical responsiveness to ultraviolet rays.

The above-mentioned separating agent can be a particulate separating agent. Examples of such particulate separating agents include particles formed only of the separating agent and particles obtained by supporting the separating agent on a particulate carrier. The separating agent can be supported on the carrier by physical adsorption or by chemical bonding to the carrier.

The separating agent can be a low molecular weight separating agent or polymer-type separating agent that exhibits an optical responsiveness. Examples of low molecular weight separating agents include ligand exchange type separating agents, charge transfer (π-π) type separating agents, hydrogen bonding type separating agents, clathrate type separating agents, ionic bonding type separating agents, intercalation type separating agents, crown ethers and derivatives thereof, and cyclodextrin and derivatives thereof. Examples of polymer type separating agents include polysaccharide derivatives, polyamides, polymethacrylate esters, polyacrylamides, proteins and tartaric acid derivatives.

Examples of the aforementioned polysaccharide derivative include polysaccharide derivatives formed of a polysaccharide and one type of group selected from aromatic ester groups, aromatic carbamoyl groups, aromatic ether groups or carbonyl groups that replace some or all of the hydroxyl groups or amino groups in the polysaccharide, which are used in separating agents for optical isomers, and examples of these include phenylcarbamate derivatives of cellulose, phenyl ester derivatives of cellulose, phenylcarbamate derivatives of amylose and phenyl ester derivatives of amylose. The phenyl groups in these derivatives may have one or more substituent groups selected from the group consisting of hydrocarbons having 1 to 20 carbon atoms and halogen atoms.

From the perspective of increasing the separation performance, the aforementioned carrier is preferably a porous material. Examples of the aforementioned carrier include synthetic polymers such as crosslinked polystyrene, crosslinked acrylic polymers and epoxy polymers, polysaccharides such as cellulose, crosslinked cellulose strengthened by crosslinking the cellulose, crosslinked agarose, crosslinked dextran and crosslinked mannan, and inorganic materials such as alumina, silica gel, mesoporous silica gel, zeolites, diatomaceous earth, fused silica, clay minerals, zirconia and metals.

The particle diameter of the separating agent can be decided according to the objects being separated by the chromatographic medium, and is preferably 10 μm or higher, more preferably 10 to 100 μm, and further preferably 20 to 100 μm. The particle diameter of the separating agent can be the average particle diameter as measured using an ordinary particle diameter measurement device, but catalog values may also be used. Meanwhile, in cases where the separating agent is used to, for example, monitor a synthesis reaction, it is possible to use a separating agent having a particle diameter of lower than 10 μm if a higher degree of separated spot separation is required. In this type of intended use, the particle diameter of the separating agent is preferably 2 to 8 μm, and more preferably 3 to 6 μm.

In cases where the chromatographic medium is a plate-shaped TLC medium, the separating agent layer can be formed by using a publicly known method used to produce a TLC plate, for example by coating a slurry that contains the aforementioned separating agent and a coating solvent on the surface of a base material serving as a support body by using a spreader, or by spraying the aforementioned slurry onto the surface of the base material serving as the support body, or by immersing (dipping) the base material serving as the support body in the aforementioned slurry that contains the separating agent and coating solvent.

In this case, if a sufficient strength can be ensured even if a base material is not present in the obtained chromatographic medium, it is possible to omit the base material and obtain a chromatograph material consisting only of a separating agent layer, a filling agent layer and a permeation layer.

In cases where the chromatographic medium is columnar, it is possible to obtain a chromatographic medium in which the permeation layer is laminated on the separating agent layer, or the permeation layer is laminated on both the separating agent layer and the filling agent layer, and a tube such as a column tube is present on the peripheral wall of the permeation layer by, for example, forming the material that constitutes the permeation layer on the inner surface of the column tube by coating or printing and then filling with a material that contains the separating agent and a binder or the like and a material that constitutes the filling agent layer so as to form the separating agent layer and the filling agent layer.

In cases where the chromatographic medium is cylindrical, it is possible to obtain a cylindrical chromatographic medium in which the separating agent layer and the filling agent layer are laminated on the base material and the permeation layer is laminated on the separating agent layer or on the separating agent layer and the filling agent layer by, for example, coating a material that contains a separating agent and a binder and a material that constitutes the filling agent layer on the peripheral surface of a rod-like base material or coating a slurry that contains a separating agent and a coating solvent on a rod-like base material and then coating a material that constitutes the filling agent layer on a region of the base material on which the slurry that contains a separating agent and a coating solvent is not present, thereby forming the separating agent layer and the filling agent layer, and then laminating the material that constitutes the permeation layer on the peripheral surface of the separating agent layer only or on the peripheral surface of the separating agent layer and the peripheral surface of the filling agent layer by coating or printing.

In addition, an example of a case in which the chromatographic medium is formed as a column without using a pre-formed base material is an embodiment such as that described below.

First, a columnar porous material having the aforementioned separating agent on at least the surface thereof is formed. This type of porous material can be formed by forming the separating agent from a columnar porous material formed of the separating agent or from a columnar porous material formed of a carrier and the aforementioned separating agent supported on the porous material, and then by laminating a layer formed of the filling agent layer on a cross-section that intersects the direction of development.

The columnar porous material formed of the separating agent can be formed by using, for example, the method disclosed in Japanese Patent Application Publication No. H4-93336, in which a porous material is formed by mixing a separating agent with plastic particles that are soluble in a solvent in which particles of the separating agent are insoluble, molding the obtained mixture by thermal press molding, and then removing insoluble plastic from the obtained molded body by means of solvent treatment.

The aforementioned columnar porous material formed of a carrier can be formed by binding carrier particles or by porosifying a columnar body formed of a carrier, and a porous material obtained by binding carrier particles can be formed using the aforementioned method in cases where the carrier particles are an organic compound such as a polymer or polysaccharide. The aforementioned porous material obtained by porosifying a columnar porous material formed of a carrier can be formed by using, for example, the method disclosed in Japanese Patent No. 3397255 or 3317749 or a so-called sol-gel method.

The separating agent can be supported on the aforementioned columnar porous material formed of a carrier by, for example, using a publicly known method for modifying the surface of pores in the porous material by physically adsorbing or chemically bonding the separating agent to the carrier.

An example of a method in which the separating agent layer is formed and the layer consisting of the filling agent layer is laminated on a cross-section that intersects the direction of development is a method in which a base material, for example, a film that is longer than the separating agent layer in the direction of development is wound on the peripheral surface of the separating agent layer to form a cylindrical void on the extension of the direction of development, a material forming the filling agent layer is introduced into the void to form the filling agent layer, and the base material is then removed.

It is possible to obtain a liquid-permeable columnar chromatographic medium by forming the permeation layer by laminating the material that constitutes the permeation layer by means of coating or printing on the peripheral surface of the columnar porous material, which has the aforementioned separating agent on at least the surface thereof and which is produced by using the procedure described above, or on the peripheral surface of the columnar porous material and the filling agent layer.

The aforementioned coating solvent can be water, an organic solvent or a mixed solvent thereof. The organic solvent can be an alcoholic solvent, a glycol ether-based solvent, a hydrocarbon-based solvent, a ketone or an ester. For example, it is possible to use $\alpha$-terpineol, butyl carbitol acetate, butyl carbitol, toluene, cyclohexane, methyl ethyl ketone or methylpropylene glycol.

As the aforementioned coating solvent, a mixed solvent of water and a water-soluble organic solvent is preferred and a mixed solvent of water and an alcohol is more preferred. The content of alcohol in the aforementioned mixed solvent is preferably 0.1 to 50 mass %, more preferably 1 to 45 mass %, and further preferably 2 to 40 mass %.

Examples of alcohols able to be used include ethanol, 1-propanol, 2-propanol, 1-butanol, 2-butanol, 2-methyl-1-propanol, 2-methyl-2-propanol, 1-pentanol and 3-methyl-3-methoxybutanol.

The content of the coating solvent in the aforementioned slurry can be decided in view of the uniformity of the formed separating agent layer, the thickness of this layer and economic factors, and is preferably 10 to 5000 parts by mass, more preferably 50 to 1000 parts by mass, and further preferably 100 to 300 parts by mass, relative to 100 parts by mass of the separating agent.

If this content falls within such a range, it is possible to use not only a slurry-like material that exhibits a high fluidity, but also a material having a low coating solvent content and a high viscosity when producing, for example, a cylindrical or columnar chromatographic medium.

From the perspective of improving the strength of the formed separating agent layer, it is preferable for the aforementioned slurry to further contain a binder. The aforementioned binder can be a component that imparts binding properties that enable a layer of the separating agent to be formed on the surface of the base material. Examples of such binders include inorganic binders such as gypsum and colloidal silica, organic fibers such as microfibrillated cellulose, thickening agents such as alkaline water-soluble copolymers, hydroxyethyl cellulose and carboxymethyl cellulose, and organic binders such as poly(vinyl alcohol) and acrylic acid. It is possible to use a single binder or a combination of two or more types thereof.

The content of the binder in the aforementioned slurry can be decided as appropriate according to the type of binder and by taking into account the strength of the formed separating agent layer and the ability to obtain a suitable ascension rate of the mobile phase in the separating agent layer. In the case of gypsum, for example, the content of the binder is preferably 0.1 to 50 parts by mass, more preferably 1 to 30 parts by mass, and further preferably 1 to 20 parts by mass, relative to 100 parts by mass of the separating agent. In addition, in the case of an organic binder such as carboxymethyl cellulose, the content of the binder is preferably 0.1 to 50 parts by mass, more preferably 0.5 to 10 parts by mass, and 1 to 5 parts by mass, relative to 100 parts by mass of the separating agent.

From the perspective of achieving satisfactory separation characteristics, the thickness of the separating agent layer in the chromatographic medium of the present invention is preferably 20 to 5000 μm, and more preferably 50 to 3000 μm.

In addition, from the perspective of maintaining good target substance separation performance, it is preferable for the thickness of the permeation layer to be less than the thickness of the separating agent layer in the chromatographic medium of the present invention.

From the perspective of maintaining a good target substance separation performance, it is preferable for the ratio of the thickness of the separating agent layer to the thickness of the permeation layer in the present invention to be such that if the thickness of the separating agent layer is 1, the thickness of the permeation layer is preferably 0.002 to 0.8, more preferably 0.005 to 0.5 and particularly preferably 0.006 to 0.4.

Meanwhile, from the perspective of maintaining a good target substance separation performance, the ratio of the thickness of the separating agent layer to the thickness of the filling agent layer in the present invention is preferably a ratio whereby the relationship between the thickness of the separating agent layer and the thickness of the filling agent layer is such that the thickness of the separating agent layer and the thickness of the filling agent layer are approximately the same or such that the filling agent layer is thinner than the separating agent layer. From such a perspective, the ratio of the thickness of the separating agent layer to the thickness of the filling agent layer in the present invention is such that if the thickness of the separating agent layer is 1, the thickness of the filling agent layer is preferably 1.0 to 0.1, more preferably 0.99 to 0.2, and particularly preferably 0.95 to 0.5.

In addition, in cases where the permeation layer is laminated so as to also face the filling agent layer, as explained below, the ratio of the thickness of the separating agent layer to the thickness of the layer obtained by combining the filling agent layer and the permeation layer is such that if the thickness of the separating agent layer is 1, the thickness of the layer obtained by combining the filling agent layer and the permeation layer is preferably 1.0 to 0.1, more preferably 0.99 to 0.2, and particularly preferably 0.95 to 0.5, from the perspective of maintaining good target substance separation performance.

The aforementioned permeation layer exhibits an optical responsiveness that is different from those of the target substances and the separating agent layer. Here, "different optical responsiveness" means that one optical response caused by irradiation by ultraviolet rays or coloration by a coloring reagent and another optical response differ in terms of the degree to which an optical recognition is possible as a result of color or brightness.

In addition, the permeation layer is a layer into which at least some of the components that form spots in the separating agent layer permeate.

In addition, it is important that the material that constitutes the permeation layer has no effect on the separation characteristics of the target substances in the separating agent layer on the chromatographic medium, that is, has no effect on the distribution of the target substances between the mobile phase and the separating agent layer, in order to prevent spots of the target substances on the chromatographic medium from becoming broad.

As a result, in cases where, for example, the separating agent used in the separating agent layer is supported on a carrier, it is preferable for the material that constitutes the permeation layer to be the same as the material of the carrier. In addition, the material that constitutes the permeation layer can be one selected as appropriate from among those materials described later that do not affect the distribution of the target substances between the mobile phase and the separating agent layer.

The aforementioned permeation layer is laminated on the separating agent layer or on both the separating agent layer and the filling agent layer, but it is preferable for the permeation layer to be laminated in a discontinuous manner in the direction of development of the chromatographic medium in order to reduce the bypass effect that is an interaction between the separating agent layer and the permeation layer, prevent spots of the target substances from becoming broad and achieve a good separation (hereinafter also referred to as separation characteristics). In the present invention, laminated in a discontinuous manner means that the aforementioned permeation layer is laminated with intervals, not laminated continuously, in the direction of development of the chromatographic medium, and these intervals may or may not be the same size.

In order to enable the permeation of the target substances and obtain sufficient resolution to detect the target substances, these intervals are preferably 0.015 mm or larger, more preferably 0.02 mm or larger, and particularly preferably 0.05 mm or larger. However, in order to suppress interactions with the separating agent layer caused by diffusion of the target substances into the permeation layer and ensure the good separation of the target substances, these intervals are preferably 4 mm or smaller, more preferably 3 mm or smaller, and particularly preferably 2 mm or smaller.

In addition, in order to enable the permeation of the target substances and ensure a sufficient area for detecting the target substances, the ratio of the volume of voids in the permeation layer (the sum of the volume of voids inside the material (internal voids) and the volume of voids among the material (external voids)) relative to the volume of the overall layer is preferably 0.1 to 0.9, and more preferably 0.2 to 0.8.

In addition, it is preferable for the permeation layer in the chromatographic medium of the present invention to be laminated in the form of dots on the aforementioned separating agent layer. In the present invention, a dot-like form is a pattern formed from a multiplicity of discontinuous points or sub-regions in shapes that may be, for example, circular, roughly circular, roughly elliptical, or a roughly polygonal shape, such as a roughly triangular or roughly quadrangular shape in which each side can be straight or curved, and the size and density of the dots is not particularly limited. From the perspective of standardizing the separation characteristics of the target substances in the chromatographic medium, it is preferable for the shape of the dots to be regular. Furthermore, it is preferable for the arrangement of the dots to be regular.

Figure 3:
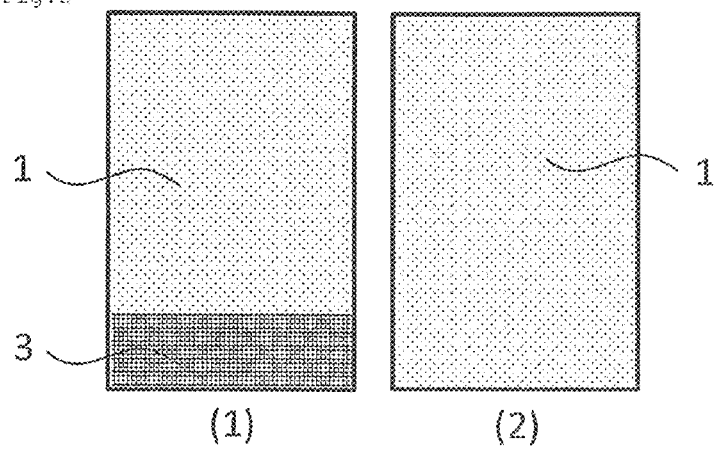
FIG. 3 is a schematic view showing a plate-like embodiment of the chromatographic medium of the present invention, FIG. 3(1) shows one embodiment in which the permeation layer is laminated only on the separating agent layer and the filling agent layer is exposed, the permeation layer is laminated in a dotted manner on the separating agent layer, FIG. 3(2) shows one embodiment in which the separating agent layer and the filling agent layer are both laminated on the permeation layer, and the permeation layer is laminated in a dotted manner.
Figure 4:
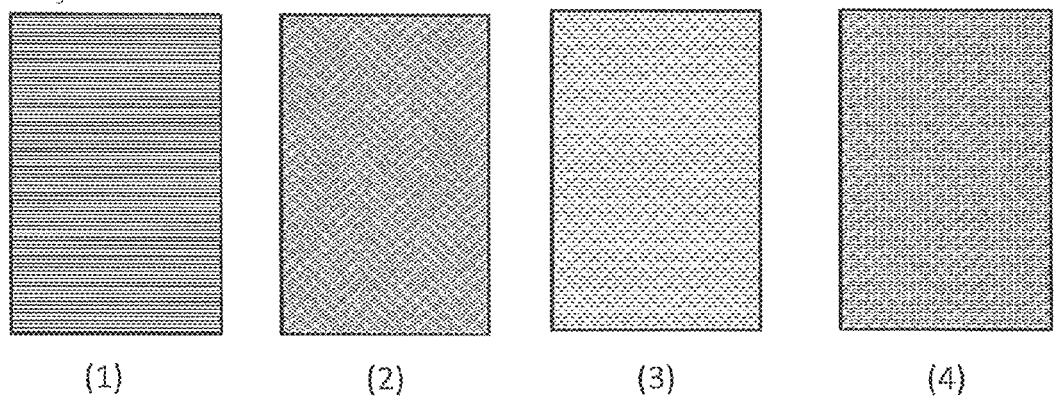
FIGS. 4(1) to 4(4) are drawings showing examples in which the permeation layer is laminated on the separating agent layer and the filling agent layer as band-like rows.
Figure 5:
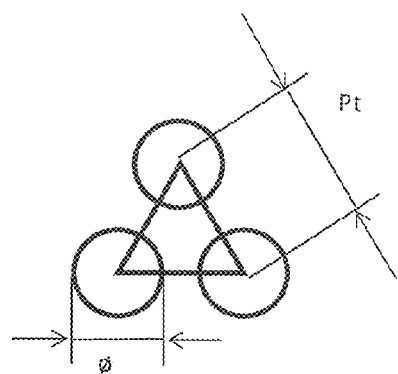
FIG. 5 is a drawing showing an example of the diameter ($\phi$) and pitch (Pt) of dots in a case where the permeation layer is laminated in the form of dots in the chromatographic medium of the present invention.

From the perspective of the permeability of the target substances, it is particularly preferable for the dots to be circular or approximately circular in shape, and from the perspective of standardizing the separation characteristics of the target substances in the chromatographic medium, as mentioned above, it is preferable for the arrangement of the dots to be regular, as shown in FIGS. 3 and 4.

In cases where the dots are circular in shape, the average diameter of the dots is preferably 0.01 to 5 mm, more preferably 0.01 to 4 mm, further preferably 0.02 to 3 mm, and particularly preferably 0.05 to 1 mm, from the perspectives of the permeability of the target substances and separation characteristics.

Meanwhile, in cases where the dots are not circular in shape, the average diameter of the maximum diameter is preferably 0.02 to 6 mm, more preferably 0.05 to 5 mm, and further preferably 0.05 to 1.5 mm, for the same reasons as those given for cases where the dots are circular in shape.

In the present invention, maximum diameter means the length of the longest axis in the case of, for example, elliptical dots, but more commonly means the maximum value of the distance between two parallel planes in cases where the shape is viewed from above and held by the two planes in an arbitrary direction.

In addition, in cases where the permeation layer is laminated in the form of dots, the interval (pitch) between the dots is preferably 0.01 to 6 mm, more preferably 0.01 to 4 mm, further preferably 0.02 to 3 mm, and particularly preferably 0.05 to 1.0 mm, from the perspectives of reducing the interactions with the separating agent layer and improving the resolution when detecting the target substances that permeate into the permeation layer.

In the cases where the dots are circular in shape, the pitch between the dots is preferably 0.01 to 6 mm, more preferably 0.02 to 3 mm, further preferably 0.05 to 1 mm, and particularly preferably 0.06 to 1 mm, for the same reasons as those given above.

In addition, when expressed in terms of lines per inch (number of dots per inch), the dot density is preferably 5 to 2000, more preferably 10 to 400, and further preferably 20 to 300.

In addition to the dot-like pattern mentioned above, a preferred embodiment of the permeation layer in the chromatographic medium of the present invention is one in which the permeation layer is laminated as band-like rows that intersect the direction of development of the chromatographic medium. By laminating in this way, it is possible to ensure the satisfactory separation characteristics of the target substances and achieve the satisfactory permeation of the target substances into the permeation layer.

The shape of the bands that form the aforementioned band-like rows can be straight lines, wavy lines or dashed lines thereof. The width of these bands is not particularly limited, but is preferably 0.01 to 15 mm, and more preferably 0.02 to 10 mm, from the perspectives of ensuring the separation characteristics of target substances and obtaining a sufficient resolution to detect the target substances.

In addition, the interval between the bands is not particularly limited, but it is preferable for the intervals between the bands to be equal from the perspective of obtaining the uniform separation characteristics of the target substances, and this interval is preferably 0.01 to 3 mm, and more preferably 0.02 to 2 mm.

The material that constitutes the permeation layer in the chromatographic medium of the present invention can be a porous material.

From the perspective of ensuring the satisfactory permeation of the target substances, this type of porous material is one in which the pore volume, as measured by a gas adsorption method, is preferably 0.1 ml/g or higher, more preferably 0.2 ml/g or higher, and particularly preferably 0.3 to 0.9 ml/g.

Porous materials having a pore volume such as that mentioned above can be a commercially available silica gel or ceramic in which the catalog value for the pore volume satisfies the range mentioned above, which are the preferred porous materials mentioned below, and it is possible to adjust the pore volume of a porous material that contains silica by treating the material with an aqueous solution of hydrogen fluoride or an aqueous solution of an alkali, and it is possible to adjust the pore volume of a ceramic by adjusting the firing conditions during granulation or treating with an acidic solution.

In addition, from the perspective of preventing the aggregation of a slurry that contains the porous material, the particle diameter of the porous material is preferably 0.1 μm or higher, more preferably 1 μm or higher, and particularly preferably 2 μm or higher. Meanwhile, from the perspectives of the permeability when screen printing a slurry containing this porous material and the finish of the surface of the permeation layer, the upper limit for the particle diameter of the porous material is preferably 100 μm or lower, more preferably 70 μm or lower, and particularly preferably 50 μm or lower.

The particle diameter of the porous material can be the average particle diameter as measured using an ordinary particle diameter measurement device, but catalog values may also be used.

Examples of porous materials able to be used in the present invention include silica gel, mesoporous silica gel, zeolites, cellulose, diatomaceous earth, fused silica, clay minerals, alumina, zirconia, other ceramics, for example ceramics obtained by subjecting a variety of clay minerals, such as sepiolite, attapulgite, palygorskite, talc, which contains $SiO_2$ and MgO as primary components, kaolinite, which contains $SiO_2$ as a primary component, and montmorillonite, to crushing, granulating, acid treatment (if necessary) and firing. It is possible to use commercially available products of these porous materials, and it is also possible to use porous materials in which catalog values for the pore volume and particle diameter are as described above.

Of these, it is preferable to use porous materials having the above-mentioned pore volume and particle diameter, and it is preferable to use silica gel from the perspective of affinity with solvents.

The types of silica gel able to be used in the present invention include silica gel that has been surface-treated with a silane coupling agent, for example silica gel that has been modified by octadecylsilyl groups or aminopropylsilyl groups. This type of surface-treated silica gel tends not to affect the distribution of the target substances between the separating agent layer and the mobile phase, and is therefore preferably used.

In addition, selecting a material that does not affect the distribution of the target substances between the separating agent layer and the mobile phase as the above-mentioned porous material is preferred from the perspective of preventing the spots of the target substances on the chromatographic medium from becoming broad.

In addition, the material that constitutes the permeation layer in the chromatographic medium of the present invention may be the fluorescent indicators or coloring reagents mentioned later. In addition, it is also possible to obtain the permeation layer by laminating a composition obtained by mixing these fluorescent indicators or coloring reagents with a binder and, if necessary, a support body having a particle diameter of 0.1 to 100 μm, such as a glass, plastic, metal or ceramic.

The content of the binder in such a composition can be decided as appropriate according to the type of binder used and by taking into account the strength of the formed permeation layer and the ability to reduce the bypass effect that is an interaction between the separating agent layer and the permeation layer in the permeation layer. In the case of gypsum, for example, the content of the binder is preferably 0.1 to 50 parts by mass, more preferably 0.5 to 30 parts by mass, and further preferably 1 to 20 parts by mass, relative to 100 parts by mass of the fluorescent indicator or coloring reagent. In addition, in the case of an organic binder such as carboxymethyl cellulose, the content of the binder is preferably 0.1 to 50 parts by mass, more preferably 0.5 to 10 parts by mass, and 1 to 5 parts by mass, relative to 100 parts by mass of the fluorescent indicator or coloring reagent.

In addition, in cases where the aforementioned support body is incorporated, the content thereof is preferably 0.1 to 0.9 parts by mass, more preferably 0.2 to 0.8 parts by mass, and particularly preferably 0.3 to 0.7 parts by mass, relative to 100 parts by mass of the fluorescent indicator or coloring reagent.

The permeation layer in the chromatographic medium of the present invention can be laminated using a variety of methods. For example, in cases where the chromatographic medium is a plate-shaped TLC medium and the permeation layer contains a porous material as a constituent material, the permeation layer can be produced by coating a slurry that contains the porous material on the separating agent layer or on the separating agent layer and the filling agent layer of the TLC plate and then drying the slurry. In addition, the same method can also be used in cases where the permeation layer is obtained from the fluorescent indicators or coloring reagents described below or from a composition that contains these fluorescent indicators or coloring reagents, a binder and, if necessary, a support body.

In the chromatographic medium of the present invention, if the permeation layer is laminated in a discontinuous manner in the direction of development of the chromatographic medium, the permeation layer can be laminated by using, for example, a printing process.

Examples of printing processes include screen printing, such as silk screen printing, and ink jet printing.

In the case of screen printing, it is possible to use, as a screen printing plate, a plate having the shape described in the above-mentioned lamination mode as the shape of the openings (a plate having discontinuous openings in the direction of development of the chromatographic medium or a plate having variously shaped dots or band-like rows as openings). It is preferable to use a screen printing process, such as silk screen printing, due to the ability to laminate the permeation layer inexpensively using a simple procedure.

In addition, in cases where the permeation layer is laminated on the separating agent layer only or on the separating agent layer and the filling agent layer, it is possible to adjust the position or area of the laminated region by using a screen printing plate having a suitable opening part. In this way, the permeation layer can be laminated in a dotted manner over the entire surface of the filling agent layer.

The material for the screen printing plate is not limited as long as a slurry that contains the porous materials described later can be used as a printing ink. An example of this type of screen printing plate is a metal mask.

Meanwhile, in cases where ink jet printing is used, it is possible to use a slurry that contains the porous materials described later as the ink used for the printing, but it is also possible to use a commonly used ink jet printing process.

Meanwhile, in the cases where a cylindrical or columnar chromatographic medium is produced, the chromatographic medium can be produced by coating a slurry that contains a porous material on the separating agent layer or on the separating agent layer and the filling agent layer, and then drying the slurry. In addition, in the cases where the permeation layer is obtained from a fluorescent indicator or coloring reagent or from a composition that contains a fluorescent indicator or coloring reagent, a binder and, if necessary, a support body, the same method can be used.

In the cylindrical or columnar chromatographic medium, if the permeation layer is laminated in a discontinuous manner in the direction of development of the chromatographic medium, the permeation layer can be laminated by using, for example, a printing process. This type of printing process can be the screen printing described above, and the screen printing plate is preferably a flexible plate having the openings described above and is preferably wound on the peripheral surface of the separating agent layer.

In the cases where this type of screen printing process is used, by providing a desired opening part, such as a character or scale mark, on the screen printing plate, the permeation layer is not laminated on that part of the permeation layer, meaning that the separating agent layer is exposed, and because the separating agent layer exhibits an optical responsiveness that is different from the permeation layer, it is possible to verify the character or scale mark when irradiating with ultraviolet rays. In this way, it is possible to increase the usefulness of the chromatographic medium.

In order to ensure satisfactory permeation and prevent the permeation layer from being affected by the optical responsiveness of the separating agent layer when detecting the spots of the target substances when using a transparent or semitransparent porous material, the thickness (average thickness) of the permeation layer obtained by coating the slurry or by the above-mentioned printing process is preferably 0.005 mm or higher, and more preferably 0.01 mm or higher.

Meanwhile, from the perspective of preventing the diffusion of the spots of target substances, the thickness (average thickness) of the permeation layer is preferably 0.2 mm or lower, and more preferably 0.15 mm or lower.

In order to laminate the permeation layer on the separating agent layer, it is possible to use the coating or printing processes described above, but in these processes, it is possible to prepare a slurry that contains a porous material, a solution that contains a fluorescent indicator or coloring reagent or a composition that contains a fluorescent indicator or coloring reagent, a binder and, if necessary, a support body, and then use this slurry, solution or composition as a coating liquid or ink.

The materials used when preparing a slurry that contains a porous material include solvents and, if necessary, binders. Such solvents and binders can be the same as those used when preparing the separating agent layer.

Examples of the above-mentioned fluorescent indicator include magnesium tungstate and manganese-containing zinc silicate, and examples of the solvents able to be used when preparing a solution or slurry that contains the above-mentioned fluorescent indicators include organic solvents, such as alcoholic solvents, glycol ether-based solvents, hydrocarbon-based solvents, ketones or esters, that are used as screen printing ink solvents. For example, it is possible to use α-terpineol, butyl carbitol acetate, butyl carbitol, toluene, cyclohexane, methyl ethyl ketone or methylpropylene glycol. In order to prevent the fluidity of the slurry from deteriorating during printing and prevent screen clogging, an appropriate solvent is selected in view of physical properties such as the fluidity, boiling point and evaporation rate.

Meanwhile, examples of coloring reagents include anisic aldehyde solutions, phosphomolybdic acid solutions, iodine solutions, ninhydrin solutions, chameleon solutions, DNPH solutions, manganese chloride solutions and bromocresol green solutions.

When using a composition that contains a fluorescent indicator or coloring reagent, a binder and, if necessary, a support body, it is possible to obtain a coating liquid or printing ink by dissolving or suspending the above-mentioned binder in a solution of the above-mentioned fluorescent indicator or coloring reagent.

When incorporating a porous material as a constituent material that forms the permeation layer, it is possible to use an organic solvent, such as an alcoholic solvent, a glycol ether-based solvent, a hydrocarbon-based solvent, a ketone or an ester, as the solvent used in the slurry that contains the porous material. For example, in cases where an alcohol is used, a mixed solvent of water and a water-soluble organic solvent is preferred and a mixed solvent of water and an alcohol is more preferred. The content of alcohol in the aforementioned mixed solvent is preferably 0.1 to 50 mass %, more preferably 1 to 45 mass %, and further preferably 2 to 40 mass %.

Examples of alcohols able to be used include ethanol, 1-propanol, 2-propanol, 1-butanol, 2-butanol, 2-methyl-1-propanol, 2-methyl-2-propanol, 1-pentanol and 3-methyl-3-methoxybutanol.

The content of the solvent in the aforementioned slurry can be decided in view of the uniformity of the formed permeation layer, the thickness of this layer and economic factors, and is preferably 10 to 5000 parts by mass, more preferably 50 to 1000 parts by mass, and further preferably 100 to 300 parts by mass, relative to 100 parts by mass of the porous material.

From the perspective of improving the strength of the formed permeation layer, it is preferable for the aforementioned slurry to further contain a binder. The aforementioned binder may be a component that imparts binding properties that enable a layer of the porous material to be formed on the surface of the separating agent layer. Examples of such binders include inorganic binders such as gypsum and colloidal silica, organic fibers such as microfibrillated cellulose, thickening agents such as alkaline water-soluble copolymers, hydroxyethyl cellulose and carboxymethyl cellulose, and organic binders such as poly(vinyl alcohol) and acrylic acid. It is possible to use a single binder or a combination of two or more types thereof.

The content of the binder in the aforementioned slurry can be decided as appropriate according to the type of binder used and by taking into account the strength of the formed permeation layer and being able to obtain a suitable ascension rate of the mobile phase from the separating agent layer to the permeation layer. In the case of gypsum, for example, the content of the binder is preferably 0.1 to 50 parts by mass, more preferably 0.5 to 30 parts by mass, and further preferably 1 to 20 parts by mass, relative to 100 parts by mass of the porous material. In addition, in the case of an organic binder such as carboxymethyl cellulose, the content of the binder is preferably 0.1 to 50 parts by mass, more preferably 0.5 to 10 parts by mass, and 1 to 5 parts by mass, relative to 100 parts by mass of the porous material.

In the cases where a porous material is contained as a constituent material of the permeation layer, when detecting spots by means of an optical responsiveness brought about by irradiation with ultraviolet rays, it is possible to impart the permeation layer with an optical responsiveness by incorporating a fluorescent indicator in the slurry that contains the porous material. This type of fluorescent indicator can be a publicly known fluorescent indicator, for example the aforementioned magnesium tungstate and manganese-containing zinc silicate. The content of the fluorescent indicator can be set within a range whereby the separation of the target substances is possible, and is preferably 0.1 to 10 parts by mass, and particularly preferably 1 to 8 parts by mass from the perspective of optimizing the contrast between the target substances and the permeation layer, relative to 100 parts by mass of the aforementioned porous material.

In addition, in the cases where a porous material is contained as a constituent material of the permeation layer, when detecting spots by means of a color-producing reaction, it is possible to impart the permeation layer with an optical responsiveness by incorporating a coloring reagent in the slurry that contains the porous material. This type of coloring reagent can be a publicly known phosphomolybdic acid, ninhydrin, or the like. The content of the coloring reagent can be set within a range whereby the separation of the target substances is possible, and is preferably 0.1 to 10 parts by mass, and particularly preferably 1 to 8 parts by mass from the perspective of optimizing the contrast between the target substances and the permeation layer, relative to 100 parts by mass of the aforementioned porous material.

As described above, the chromatographic medium of the present invention has a filling agent layer which is used to fix the aforementioned target substances before the aforementioned target substances are separated.

In the present invention, "fix" means that the target substances applied as spots prior to separation are sufficiently immobilized in the region where the target substances are applied, for subsequent development by a developing solution to occur. In cases where the permeation layer is laminated on the filling agent layer in the chromatographic medium, "fix" means that the target substances are immobilized in a region that includes the permeation layer and the filling agent layer below this permeation layer, and in the cases where the filling agent layer is exposed, "fix" means that the target substances applied as spots on the filling agent layer are immobilized in that region of the filling agent layer to which the target substances were applied as spots.

The material used to constitute the filling agent layer in the chromatographic medium of the present invention can be the same as the above-mentioned materials used to constitute the permeation layer, examples of which include porous materials such as silica gel, mesoporous silica gel, zeolites, cellulose, diatomaceous earth, fused silica, clay minerals, alumina, zirconia and other ceramics. In addition, the use of materials that do not exhibit the target substance separation properties as the material that constitutes the filling agent layer is preferred from the perspective of satisfactorily achieving the effect of the present invention.

It is preferable for the above-mentioned silica gel to be surface-treated in the manner described above.

In addition, the particle diameter range of the porous materials able to be used can be the range mentioned as being suitable for the particle diameter range of the material that constitutes the permeation layer.

In addition, the porous material used in the permeation layer and the porous material used in the filling agent layer may be the same or different. In the cases where the permeation layer is also laminated on the filling agent layer by combining the material used in the filling agent layer with the material used in the permeation layer, a combination is preferred whereby interactions, such as those that can impair the development of the target substances fixed on the filling agent layer, do not occur.

In cases where a porous material is used as the material that constitutes the filling agent layer in the chromatographic medium of the present invention and a slurry is prepared in order to laminate this porous material, the solvent used in this slurry can be the same as the solvents able to be used in order to constitute the permeation layer.

In addition, the content of the solvent in the aforementioned slurry can be decided in view of the uniformity of the formed filling agent layer, the thickness of this layer and economic factors, and is preferably 10 to 5000 parts by mass, more preferably 50 to 1000 parts by mass, and further preferably 100 to 300 parts by mass, relative to 100 parts by mass of the porous material.

From the perspective of improving the strength of the formed filling agent layer, it is preferable for the aforementioned slurry to further contain a binder.

The aforementioned binder can be a component that imparts binding properties that enable a layer of the porous material to be formed in the filling agent layer. This type of binder can be the same as that used to constitute the permeation layer, and it is possible to use one such binder or two or more types thereof.

The content of the binder in the aforementioned slurry can be decided as appropriate according to the type of binder and by taking into account the strength of the formed filling agent layer and the ability to obtain a suitable development speed of the mobile phase in the filling agent layer. In the case of gypsum, for example, the content of the binder is preferably 0.1 to 50 parts by mass, more preferably 0.5 to 30 parts by mass, and further preferably 1 to 20 parts by mass, relative to 100 parts by mass of the porous material. In addition, in the case of an organic binder such as carboxymethyl cellulose, the content of the binder is preferably 0.1 to 50 parts by mass, more preferably 0.5 to 10 parts by mass, and further preferably 1 to 5 parts by mass, relative to 100 parts by mass of the porous material.

In addition, the above-mentioned filling agent layer, like the permeation layer, may contain a fluorescent indicator or coloring reagent, and may be a layer consisting only of these components. Fluorescent indicators and coloring reagents able to be used, and the usage forms thereof, can be the same as those given as examples for the permeation layer.

In cases where the chromatographic medium of the present invention is a plate-like chromatographic medium, the method for laminating the filling agent layer can be a method whereby, for example, the separating agent layer is laminated on apart of the base material in advance, and a slurry containing the material that constitutes the filling agent layer is coated or sprayed, by means of a spreader, on that part of the surface of the base material where the separating agent layer is not laminated. Alternatively, in cases where the same material constitutes the permeation layer and the separating agent layer, it is possible to laminate the separating agent layer on a part of the base material in advance, laminate a slurry that contains the material that constitutes the permeation layer and the filling agent layer on the surface of the base material where the separating agent layer is laminated by means of a coating, spraying or printing technique using a method that is the same as the aforementioned methods used to laminate the permeation layer, thereby forming a layer laminated on the separating agent layer as the permeation layer and forming a layer laminated on the base material as the filling agent layer. In this way, the permeation layer and the filling agent layer can be formed simultaneously. In such cases, the filling agent layer has a single layer structure and the permeation layer and filling agent layer can be obtained in a single step.

Meanwhile, in cases where the chromatographic medium of the present invention is columnar, it is possible to, for example, form the permeation layer along the inner wall surface of a column tube, and then fill the material that constitutes the filling agent layer inside the tube either before or after forming the separating agent layer, as described above. In the case of a cylindrical chromatographic medium also, it is possible to coat the material that constitutes the filling agent layer on the peripheral surface of the base material, as described above. In the case of a cylindrical chromatographic medium having no base material also, it is possible to use a method in which a columnar porous material having the aforementioned separating agent on at least the surface thereof is formed, a base material, for example, a film that is longer than the separating agent layer in the direction of development is wound on the peripheral surface of the separating agent layer to form a cylindrical void on the extension of the direction of development, and a material forming the filling agent layer is introduced into the void to form the filling agent layer, as described above.

Moreover, from the perspective of adequately fixing the target substances, the thickness of the filling agent layer in the chromatographic medium of the present invention in cases where the permeation layer is laminated is preferably 2 to 5000 µm, and more preferably 5 to 3000 µm, in terms of the total thickness of the filling agent layer and the permeation layer.

Figure 8:
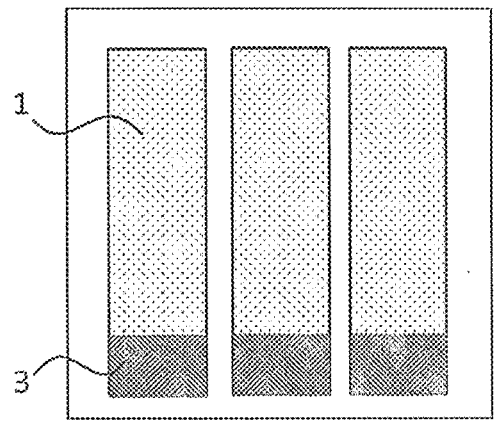
FIG. 8 is a schematic view showing a TLC plate in which the chromatographic medium of the present invention is laminated in a plurality of regions on a single base material.

In addition, the present invention also provides a TLC plate in which the above-mentioned chromatographic medium is laminated in a plurality of regions on a single base material (see FIG. 8). According to this type of TLC plate, it is possible to laminate various combinations of separating agent layers and permeation layers on a single base material, and also possible to observe target substance separation characteristics using a single developing solution. With regard to the method of laminating the separating agent layer, the filling agent layer and the permeation layer, in the case of a plurality of target chromatograph media, it is possible for layers to be overlaid in such a way as to be in contact with each other, but it is also possible to use the method described above.

Figure 9:
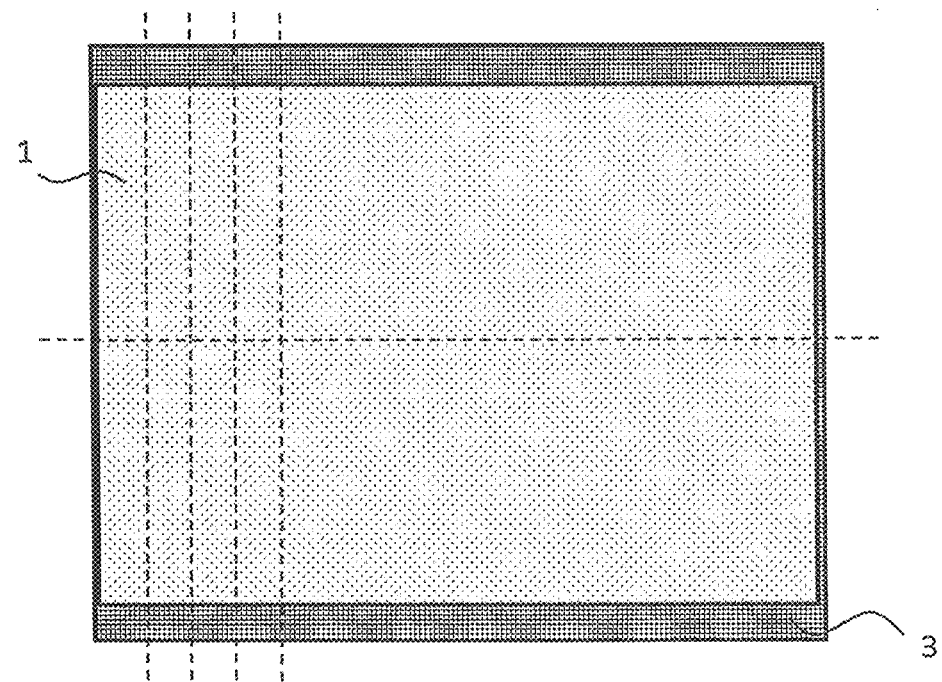
FIG. 9 is a schematic view showing a TLC material that contains the chromatographic medium of the present invention and a base material as constituent elements.

In addition, the present invention also provides a TLC material in which a separating agent layer, a filling agent layer and a permeation layer are laminated on a single base material and which has a region in which the permeation layer is not laminated on the edges of the base material, as shown schematically in FIG. 9 (see FIG. 9). According to this type of TLC material, it is possible to obtain the TLC plate shown in FIG. 3(1), which has a base material, a separating agent layer, a filling agent layer and a permeation layer and in which the filling agent layer is exposed, by, for example, providing grooves at the positions shown by the dashed lines in FIG. 9 and cutting this TLC material along these grooves by using an appropriate method, such as snapping by hand or cutting with a plate cutter.

For the base material, separating agent layer and permeation layer used here and the methods for laminating these layers, it is possible to use the features described above. In addition, the positions where the grooves are provided in the TLC material are not particularly limited.

The chromatographic medium of the present invention can achieve separation and detection of the target substances in a sample by using a method that is essentially the same as the methods that use conventional TLC plates even though the shape of the medium varies from aspect to aspect.

The separation and detection of the target substances in a sample can be achieved by using a method that includes a step of developing the sample by using a mobile phase in the direction of development of the chromatographic medium (in cases where the chromatographic medium is a TLC plate, this direction is preferably the longitudinal direction when using a rectangular medium), a step of drying the mobile phase on the chromatographic medium, and a step of detecting the spots of the migrated components of the target substances by irradiating with ultraviolet rays or by coloration treatment using a coloring reagent.

By developing a sample with a mobile phase by using the chromatographic medium of the present invention, the target substances in the sample are separated as the target substances permeate into the permeation layer on the separating agent layer.

Moreover, the target substances in the present invention exhibit an optical responsiveness that is different from those of the permeation layer and exhibit an optical responsiveness that is the same as those of the separating agent layer.

By using the chromatographic medium of the present invention, it is possible to achieve the separation and optical detection of the extract component and the raffinate component of the target substances in the sample using a single chromatography process. Comparing with a conventional TLC plate having two separating agent layers, the conventional plate had the problem of the target substance peaks becoming broad due to differences in the migration rates of the components of the target substances in the sample between the separating agent layers, whereas with the present invention, this type of problem does not occur and the raffinate component and extract component can both be reliably detected. In addition, if the chromatographic medium of the present invention has a plate-like shape, it is possible to reliably detect the state of separation of each sample when the spots of a plurality of samples are applied in a line and developed simultaneously. In addition, it is possible to select a region (including the separating agent layer) that includes a specific spot that has permeated into the permeation layer and use this region to isolate components of the target substances by carrying out an extraction process.

EXAMPLES

Example 1

Firstly, a first slurry was prepared by adding 3.00 g of a Chiralpak IA (registered trademark) manufactured by Daicel Corporation ("IA Filler"), 0.45 g of gypsum, 3.00 g of an aqueous solution containing 2% of 1110 grade CMC (carboxymethyl cellulose, manufactured by Daicel Corporation)

and 0.45 g of an aqueous solution containing 20% of Snowtex C (manufactured by Nissan Chemical Industries, Ltd.) to a mixed solution containing 0.30 g of water and 1.20 g of ethanol, and then stirring vigorously while irradiating with ultrasonic waves.

In addition, a second slurry was prepared by adding 2.00 g of silica gel (IR-60-5/20-U, liquid chromatography grade manufactured by Daiso), 0.10 g of gypsum, 3.00 g of an aqueous solution containing 2% of 1110 grade CMC (carboxymethyl cellulose, manufactured by Daicel Corporation), 0.02 g of a manganese-containing zinc silicate, and 0.30 g of an aqueous solution containing 20% of Snowtex C (manufactured by Nissan Chemical Industries, Ltd.) to a mixed solution containing 1.01 g of water and 1.40 g of ethanol, and then stirring vigorously while irradiating with ultrasonic waves.

Furthermore, a third slurry was prepared by adding 1.00 g of silica gel (IR-60-5/20-U, liquid chromatography grade manufactured by Daiso), 0.05 g of gypsum, 1.50 g of an aqueous solution containing 2% of 1110 grade CMC (carboxymethyl cellulose, manufactured by Daicel Corporation), 0.04 g of a manganese-containing zinc silicate and 0.15 g of an aqueous solution containing 20% of Snowtex C (manufactured by Nissan Chemical Industries, Ltd.) to a mixed solution of 0.06 g of water and 0.55 g of ethanol and then stirring vigorously while irradiating with ultrasonic waves.

Of these slurries, the first slurry and the second slurry were uniformly coated on the surface of 6 glass plates arranged in series by means of a TLC plate preparation spreader in such a way that the first slurry was uniformly coated on that part of the surface other than a region extending from the dip end part that was dipped in a developing solution and having a length of 20 mm, and the second slurry was coated on the region extending from the dip end part that was dipped in the developing solution and having a length of 20 mm. The first slurry layer and second slurry layer were then air dried and vacuum dried at 60° C. for 3 hours by using a vacuum pump, thereby laminating a separating agent layer consisting of the first slurry and laminating a filling agent layer consisting of the second slurry in such a way as to come into contact with the aforementioned separating agent layer via a plane that intersects the direction of development in the aforementioned TLC plate.

In addition, the third slurry was coated on the separating agent layer and filling agent layer using a metal mask (manufactured by Tokyo Process Service Co. Ltd.). A plate having regular circular openings with diameters of 0.4 mm at a pitch of 0.6 mm (see FIG. 7) was used as a screen printing plate. The third slurry layer that formed the permeation layer was then air dried and vacuum dried at 60° C. for 3 hours by using a vacuum pump, thereby producing a TLC plate 1 in which the permeation layer was laminated in a dotted manner on the separating agent layer and filling agent layer.

The TLC plate 1 had a width of 5 cm and a length of 10 cm. In this way, the filling agent layer was present in a region extending from the bottom edge of the TLC plate and having a length which is 1/5th of the length of the TLC plate in the direction of development (up to 2.0 cm from the bottom edge of the TLC plate). In the TLC plate 1, the thickness of the separating agent layer was 150 μm, the thickness of the filling agent layer was also 150 μm and the thickness of the permeation layer was 20 μm.

The separating agent layer formed of the first slurry was a layer formed of the IA filler, and the filling agent layer formed of the second slurry and the permeation layer formed of the third slurry were layers of the aforementioned silica gel. In addition, the average particle diameter of the IA filler was 20 μm and the average particle diameter of the silica gel was 14.4 μm.

Approximately 3 μL of an ethyl acetate solution containing 1% of a racemate of trans-stilbene oxide (t-SO), 1% of a racemate of Tröger's base (TB) and 1% of a racemate of a flavanone (FLV) was applied as a spot to a position approximately 1 cm from the bottom, if the direction of development of the TLC plate 1 is taken to be vertical (a region of the filling agent layer). The TLC plate 1 was placed, with the sample spot downwards, in a developing bath containing a mixed solvent of n-hexane and ethanol at a volume ratio of 9:1 as a developing solution, and optical isomers of the trans-stilbene oxide, Tröger's base and flavanone in the sample were developed in the direction of development of the TLC plate 1.

Following this developing, the TLC plate 1 was dried with cold air, and when the TLC plate 1 was irradiated with ultraviolet rays, spots of the raffinate component (Rt-SO) and extract component (Et-SO) of trans-stilbene oxide, spots of the raffinate component (RTB) and extract component (ETB) of Tröger's base, and spots of the raffinate component (RFLV) and extract component (EFLV) of the flavanone were confirmed as dark brown-black spots on the permeation layer (see FIG. 1).

The Rf value for each spot was determined from the position at which the sample was applied on the permeation layer, the position reached by the developing solution and the position of the center of the spot. Furthermore, the k' value was determined from the relationship k'=(1−Rf)/Rf. Furthermore, the α value was determined by using the k' value. The results for these optical isomers are shown in Table 1.

Comparative Example 1

A TLC plate 3 was prepared using the same raw materials and procedure as those used in Example 1, except that the filling agent layer was not provided on the TLC plate of Example 1 and the permeation layer was provided over the entire surface of the separating agent layer. In addition, optical isomers of the trans-stilbene oxide, Tröger's base and flavanone were developed using the same procedure and developing solution as those used in Example 1, except that the spotting of the target substances was carried out on the permeation layer. Next, the Rf value for each spot was determined in the same way as in Example 1 from the position at which the sample was applied on the permeation layer, the position reached by the developing solution and the position of the center of the spot. Furthermore, the k' value was determined from the relationship k'=(1−Rf)/Rf. Furthermore, the α value was determined by using the k' value. The results for these optical isomers are shown in Table 1.

TABLE 1

|  | Example 1 | | | Comparative Example 1 | | |
| --- | --- | --- | --- | --- | --- | --- |
|  | t-SO | TB | FLV | t-SO | TB | FLV |
| Rf1 | 0.44 | 0.26 | 0.25 | 0.66 | 0.48 | 0.44 |
| Rf2 | 0.35 | 0.21 | 0.16 | 0.58 | 0.41 | 0.34 |
| α | 1.46 | 1.32 | 1.75 | 1.41 | 1.33 | 1.53 |
| k'1 | 1.27 | 2.85 | 3.00 | 0.52 | 1.08 | 1.27 |
| k'2 | 1.86 | 3.76 | 5.25 | 0.72 | 1.44 | 1.94 |

Example 2

Optical isomers of the trans-stilbene oxide, Tröger's base and flavanone in the sample were developed in the direction of development of the TLC plate 1 using the same procedure as that used in Example 2, except that a TLC plate 2, which was prepared using the same raw materials and procedure as those used for TLC plate 1 prepared in Example 1, was used and methanol was used as the developing solution. Next, the Rf value, k' value and α value for each spot was determined in the same way as in Example 1 from the position at which the sample was applied on the permeation layer, the position reached by the developing solution and the position of the center of the spot. The results for these optical isomers are shown in Table 2.

Comparative Example 2

A TLC plate 4 was prepared using the same raw materials and procedure as those used in Example 1, except that the filling agent layer was not provided on the TLC plate of Example 1 and the permeation layer was provided over the entire surface of the separating agent layer. In addition, optical isomers of the trans-stilbene oxide, Tröger's base and flavanone were developed using the same procedure as that used in Example 1, except that the spotting of the target substances was carried out on the permeation layer and methanol was used as the developing solution. Next, the Rf value for each spot was determined in the same way as in Example 1 from the position at which the sample was applied on the permeation layer, the position reached by the developing solution and the position of the center of the spot. Furthermore, the k' value was determined from the relationship k'=(1−Rf)/Rf. Furthermore, the α value was determined by using the k' value. The results for these optical isomers are shown in Table 2.

TABLE 2

|     | Example 2 | | | Comparative Example 2 | | |
| --- | --- | --- | --- | --- | --- | --- |
|     | t-SO | TB | FLV | t-SO | TB | FLV |
| Rf1 | 0.44 | 0.40 | 0.40 | 0.55 | 0.50 | 0.46 |
| Rf2 | 0.40 | 0.29 | 0.28 | 0.48 | 0.39 | 0.35 |
| α | 1.18 | 1.63 | 1.71 | 1.32 | 1.56 | 1.58 |
| k'1 | 1.27 | 1.50 | 1.50 | 0.82 | 1.00 | 1.17 |
| k'2 | 1.50 | 2.45 | 2.57 | 1.08 | 1.56 | 1.86 |

From the results obtained in Examples 1 and 2 and Comparative Examples 1 and 2, it was understood that good target substance separation characteristics are obtained in the cases where the filling agent layer is provided in a specific length range in the direction of development from the bottom edge of the TLC plate and the target substances are developed after being applied to this filling agent layer.

INDUSTRIAL APPLICABILITY

TLC has been used in the past as important means for investigating the separation conditions in column chromatography and has also been used to isolate target substances. Because the present invention enables the state of separation of the target substances to be detected more reliably and simply than in the past by using a separating agent, by which detection of the state of separation by optical response characteristics was difficult, it is expected that the present invention will contribute to a further expansion of applications for this type of separating agent and to a further development of separation and purification techniques that use this type of separating agent.

EXPLANATION OF REFERENCE NUMERALS t-SO: trans-stilbene oxide
TB: Tröger's base
FLV: Flavanone
1: Permeation layer
2: Separating agent layer
3: Filling agent layer
4: Base material
5: Direction of irradiation with ultraviolet rays
6, 6': Spotting direction

The invention claimed is:

1. A chromatographic medium comprising:
   a separating agent layer, which is used to separate target substances;
   a filling agent layer, which is used to fix the target substances before the target substances are separated; and
   a permeation layer, which is disposed in a different plane from the separating agent layer, used to enable permeation of the target substances separated by the separating agent layer and contains a porous material and a fluorescent indicator or coloring reagent as constituent materials,
   wherein the permeation layer is laminated to a region of a surface of the separating agent layer or to a region of a surface of the filling agent layer by applying a slurry containing the porous material and the fluorescent indicator or coloring reagent and then drying the slurry and not laminated to another region of the surface of the separating agent layer or another region of the surface of the filling agent layer, the filling agent layer comes into contact with the separating agent layer at a plane that is approximately perpendicular to a direction of development of the target substances in the chromatographic medium and is positioned on an upstream side in the direction of development,
   the separating agent layer exhibits a separability of the target substances and exhibits an optical responsiveness to ultraviolet rays, and
   the permeation layer exhibits an optical responsiveness that is different from those of the target substances and the separating agent layer.

2. The chromatographic medium according to claim 1, wherein the filling agent layer is laminated in a region of the chromatographic medium extending from a bottom edge of the chromatographic medium and having a length which is 1/20 to 1/2 of the length of the chromatographic medium in the direction of development.

3. The chromatographic medium according to claim 1, wherein the permeation layer is laminated in the form of dots on the separating agent layer.

4. The chromatographic medium according to claim 3, wherein in the permeation layer laminated in the form of dots, the average diameter of the dots is 0.01 to 5 mm and the pitch between dots is 0.015 to 5 mm.

5. The chromatographic medium according to claim 1, wherein the permeation layer is laminated on the separating agent layer as band-like rows that intersect a direction of development of the chromatographic medium.

6. The chromatographic medium according to claim 5, wherein bands that form the band-like rows are selected from among straight lines, wavy lines and dashed lines thereof.

7. The chromatographic medium according to claim 1, wherein the permeation layer is thinner in depth than the separating agent layer.

8. The chromatographic medium according to claim 1, wherein a separating agent that constitutes the separating agent layer is a separating agent for optical isomers.

9. The chromatographic medium according to claim 8, wherein the separating agent for optical isomers contains a polysaccharide derivative formed of a polysaccharide and one type of group selected from the group consisting of aromatic ester groups, aromatic carbamoyl groups, aromatic ether groups and carbonyl groups that replace some or all of hydroxyl groups or amino groups in the polysaccharide.

10. The chromatographic medium according to claim 1, wherein the filling agent layer contains a porous material as a constituent material.

11. The chromatographic medium according to claim 10, wherein the permeation layer is laminated in a discontinuous manner in the direction of development of the chromatographic medium.

12. The chromatographic medium according to claim 1, wherein the porous material is silica gel or surface-treated silica gel.

13. The chromatographic medium according to claim 1, wherein the permeation layer further comprises a binder as a constituent material.

14. The chromatographic medium according to claim 1, wherein scale marks and/or characters are present on the permeation layer.

15. The chromatographic medium according to claim 14, wherein the scale marks and/or characters exhibit optical responsiveness that are different from those of the permeation layer.

16. The chromatographic medium according to claim 1, additionally comprising a base material which faces the separating agent layer or the permeation layer.

17. The chromatographic medium according to claim 1, wherein the chromatographic medium is plate-shaped, cylindrical or columnar.

18. A TLC plate comprising:
the chromatographic medium according to claim 1; and
a base material used to support the chromatographic medium,
wherein the chromatographic medium is laminated on a plurality of regions on the base material.

19. A TLC material comprising:
the chromatographic medium according to claim 1; and
a base material used to support the chromatographic medium.

* * * * *